United States Patent [19] [11] 4,024,129
Henniger et al. [45] May 17, 1977

[54] PROCESS FOR THE PREPARATION OF HETEROCYCLIC COMPOUNDS

[75] Inventors: Peter Wolfgang Henniger, Leiden; Antoon Van Harrewijn, Delft, both of Netherlands

[73] Assignee: Gist-Brocades N.V., Delft, Netherlands

[22] Filed: Nov. 3, 1971

[21] Appl. No.: 195,488

[30] Foreign Application Priority Data

Nov. 6, 1970 United Kingdom ............ 53039/70

[52] U.S. Cl. .................... 260/239.1; 260/243 C; 260/557 R; 260/558 R; 260/558 P; 260/561 R; 260/562 R

[51] Int. Cl.[2] ............ C07D 499/04; C07D 501/02

[58] Field of Search ........ 260/239.1, 243 C, 558 R, 260/558 P

[56] References Cited

UNITED STATES PATENTS 3,144,452 8/1964 Wild et al. ...................... 260/248

OTHER PUBLICATIONS

Chem. Abstracts 68:68325u, (1968).
Chem. Abstracts 69:105631j, (1968).
Chem. Abstracts 74:41694a, (1971).

*Primary Examiner*—G. Thomas Todd
*Attorney, Agent, or Firm*—Hammond & Littell

[57] ABSTRACT

A process for the preparation of acylamido derivatives by reaction of a compound of the formula Z - N = C = O, wherein Z is an optionally substituted alkyl-, aryl- (preferably phenyl or naphthyl) or cycloalkyl or optionally substituted heterocyclic, preferably a penicillanic acid or a cephalosporanic acid nucleus, having carboxyl groups and an optionally present hydroxy group protected, with a carboxylic acid of the formula

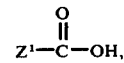

wherein $Z^1$ is an optionally substituted hydrocarbon group, in the presence of a catalyst selected from the group consisting of substituted pyridines and their N-oxides, optionally substituted imidazoles or their N-oxides, optionally substituted benzimidazoles or their N-oxides, and optionally substituted imidazo [1,2-α] pyridines or their N-oxides.

10 Claims, No Drawings

PROCESS FOR THE PREPARATION OF HETEROCYCLIC COMPOUNDS

STATE OF THE ART

In the reaction of isocyanates with carboxylic acids, basic catalysts such as pyridine and triethylamine have been employed to favor the production of the amide product. Such basic catalysts, particularly pyridine, have been used in the production of cephalosporins and penicillins from the corresponding 6-isocyanato-penicillanic acid esters or 7-isocyanato-cephalosporanic àcid esters by reaction with carboxylic acids, but the use of these catalysts has often resulted in side reactions with the production of ureas occuring to an undesired extent.

The reaction scheme illustrates schematically the reactions which occur when a 6-isocyanato-penicillanic acid or 7-isocyanato-cephalosporanic acid, in which the carboxyl group is protected, is reacted with a carboxylic acid.

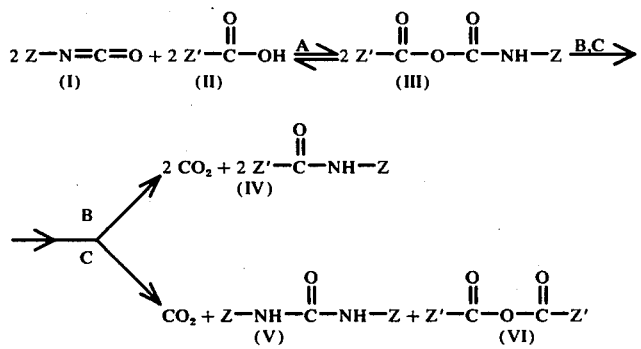

wherein Z is a penicillanic acid or a cephalosporanic acid nucleus with the carboxyl group protected such as by a trialkylsilyl, benzyl or phenacyl group and, in the case of cephalosporanic acid, the hydroxyl group is protected also, and Z' is an unsubstituted or substituted hydrocarbon group, with the carbon atom in α-position to the carboxyl group (formula II) being saturated, i.e. not linked to another carbon atom by a double or triple bond, or forming part of an aryl ring, and the hydrocarbon group carries no substituent more reactive to the isocyanate group than the carboxyl group itself. Reaction A between the isocyanate of formula I and carboxylic acid of formula II gives the mixed anhydride of formula III, which by route B yields the desired amide reaction product of formula IV and through route C, the undesired side reaction, a urea and an anhydride. By limiting or suppressing the formation of ureas and anhydrides by the undesired side. reaction illustrated above as route C, the yields of acyl derivatives of 6-aminopenicillanic acid or 7-aminocephalosporanic acid of formula IV can be increased.

OBJECTS OF THE INVENTION

It is an object of the invention to provide a novel process for the preparation of amides from isocyanates and carboxylic acids.

It is a further object of the invention to provide a novel process for the preparation of amides using heterocyclic catalysts which have not been previously used.

These and other objects and advantages of the invention will become obvious from the following detailed description.

THE INVENTION

The novel process of the invention for the preparation of acyl amides comprises reacting an isocyanate compund of the formula $$Z-N=C=O$$

wherein Z is selected from the group consisting of optionally substituted alkyl, aryl, cycloalkyl, the substituents not interfering with the reaction and optionally substituted heterocycles having any carboxyl and hydroxy groups protected with a carboxylic acid of the formula

   A wherein Z' is an hydrocarbon optionally substituted with a substituent less reactive with the isocyanato compound than the carboxylgroup, with the carbon atom α-to the carboxyl group being saturated, in the presence of a catalyst having a formula selected from the group consisting of A) 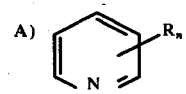   I wherein R is at least one electron releasing group selected from the group consisting of lower alkoxy, aryloxy, aryl lower alkoxy, silyloxy, di lower alkylamino, silyl lower alkylamino and disilylamino with the proviso that there are not electron releasing groups in both the 2-and 6-positions and n is 1, 2 or 3 and N-oxides thereof, B) 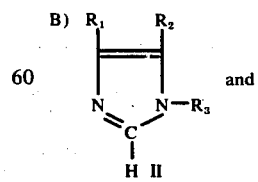 and 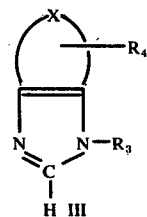

wherein $R_1$ and $R_2$ are selected from the group consisting of hydrogen, lower alkyl, lower alkenyl, lower alkoxy, aryl, aryloxy, aryl lower alkoxy, silyloxy, di lower alkylamino, silyl lower alkylamino, disilylamino and halogen and $R_3$ is selected from the group consisting of aliphatic hydrocarbon, lower alkoxy, silyl, cycloalkyl, aryl and aryl aliphatic hydrocarbon, X is the residue of a hydrocarbon ring which may contain C=C linkages and $R_4$ at least one member of the group consisting of hydrogen, lower alkyl, lower alkenyl, lower alkoxy, aryl, aryloxy, aryl lower alkoxy, silyloxy, di lower alkylamino, silyl lower alkylamino, disilylamino, halogen and nitro and N-oxides thereof and C) 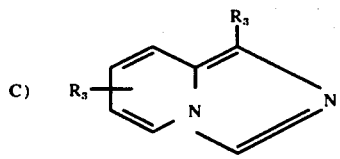 IV wherein $R_3$ has the above definition and N-oxides thereof.

The said catalysts have the effect of increasing the ratio of route B discussed above in relation to route C with the production in most instances of a greater yield of the amides than has been possible using pyridine and triethylamine as catalysts. Examples of the group Z representing heterocyclic cycles are those, such as furyl, thienyl, isoxazolyl, oxazolyl, isothiazolyl, thiadizolyl, oxadiazolyl. Examples of suitable substituents of the group Z are those, such as a halogen atom, a nitro-, cyano-, aryloxy-, alkoxy-, alkylmercapto-, arylmercapto-, protected carboxyl-, protected OH- such as a silyloxy, acylamino or a carbamoylgroup. Suitable substituents of the group Z' can be for example a halogen atom, a nitro-, cyano-, lower alkyl-, lower alkylmercapto-, alkoxy-, aryloxy-, arylmercapto-, an esterified carboxyl-, carbamoyl-, lower acylamino-, a sulphonyl, phosphonyl or phosphinyl group.

While the improved process is useful for the general reaction of carboxylic acids with isocyanates to give higher yields of amides, the process is particularly useful in the production of acyl derivatives of 6-amino penicillanic acid and 7-amino-cephalosporanic acid.

Examples of suitable substituted pyridines of formula I are those pyridines having an electron releasing group in the 4-position such as 4-methoxy-pyridine, 4-phenoxy pyridine, 4-benzyloxypyridine and 4-dimethylaminopyridine and their N-oxides. Preferably, n is 1 or 2. The term silyl as used in the specification is meant to mean a trilower alkyl silyl group.

In the catalysts of formulae II, III and IV, $R_1$ and $R_2$ and $R_4$ are alkyl of 1 to 7 carbon atoms, such as ethyl or methyl, alkenyl of 2 to 7 carbon atoms such as vinyl or allyl, alkoxy of 1 to 7 atoms such as methoxy, monocyclic aryl such as phenyl and tolyl, aryloxy such as phenoxy, aryl lower alkoxy such as benzyloxy, silyloxy, di lower alkylamino, silyl lower alkylamino, disilylamino, halogens and in the case of $R_4$ nitro. $R_3$ is preferably lower alkyl and lower alkoxy of 1 to 7 carbon atoms, lower alkenyl of 2 to 7 carbon atoms, trimethyl silyl, cycloalkyl of 4 to 7 carbon atoms, aryl such as phenyl and arylaliphatic such as benzyl or styryl, X is preferably alkylene of 4 carbon atoms which may contain double bonds. The aryl groups may be substituted such as lower alkoxy, e.g. methoxy.

Examples of specific compounds of formulae II and III are 1-methyl-imidazole, 1-benzylimidazole, 1-vinylimidazole, 5-chloro-1-methylimidazole, 1-methyl-benzimidazole, 1-isopropylbenzimidazole, 1-benzylbenzimidazole, 5-methoxy-1-phenylbenzimidazole and 5(or 6)-nitro-1-methylbenzimidazole. An example of a catalyst of Example IV is imidazol [1,2-α] pyridine.

In a preferred mode of the process of the invention, 6-aminopenicillanic acid and 7-aminocephalosphoranic acid derivatives of the formula:-

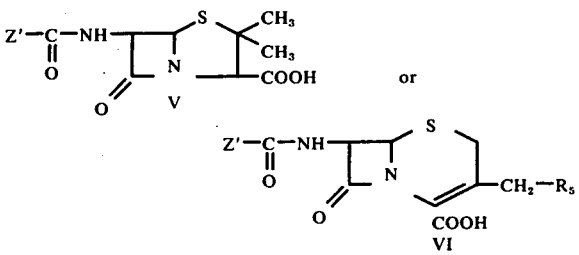

wherein Z' is as hereinbefore defined and $R_5$ is a hydrogen atom, a hydroxyl group or a lower acyloxy (preferably acetoxy) group, a prepared by reacting 6-isocyanatopenicillanic acid with its carboxy group protected (preferably by a silyl group), or a 7-isocyanatocephalosporin of the formula:-

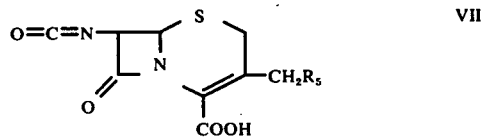

with its carboxyl group, and hydroxyl group ($R_5$) when present, protected (preferably by a silyl group), with a carboxylic acid of the formula:-

Z'—COOH        A wherein Z' is as hereinbefore defined, in the presence of a catalyst of formula I,II,III or IV or an N-oxide therefore, and removing by methods known per se the group protecting the carboxyl group, and/or hydroxyl group, from the resulting 6-acylated aminopenicillanic or 7-acylated aminocephalosporanic acid compound. When the protecting group is a silyl group, such a group is removed by hydrolysis and when it is benzyl or benzhydryl the protecting group is removed by hydrogenation and when the protecting group is a phenacylgroup, which may carry a halogen substituent (preferably in the paraposition of the benzene ring) this group can be removed by treatment with basic or nucleophilic agents. With the aforesaid catalysts, route B in the foregoing reaction scheme is appreciably more favoured at the cost of route C and, moreover, the equilibrium A may be reached more rapidly resulting in a higher yield of the desired amide product than hitherto obtainable using pyridine and triethylamine as catalyst.

The reaction is preferably carried out at temperatures between −10° to 50° C and in an inert organic solvent, such as toluene, benzonitrile, methylene chloride and methyl benzoate. Generally the use of highly anhydrous or aprotic conditions is preferred but sometimes, especially with N-oxide catalysts, better reaction conditions are obtained when a small trace of water is present, for example, water of crystallization tightly bound to the catalyst.

Preferred carboxylic acids of formula A for reacting with 6-isocyanatopenicillanic acid or 7- isocyanatocephalosporins are those of the general formula:-

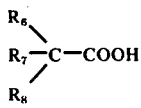

VIII wherein $R_6$ is hydrogen, a lower alkyl such as methyl or ethyl, or a halogen, $R_7$ is hydrogen, lower alkyl, cycloalkyl of 3 to 8 carbon atoms, aryl group such as phenyl, naphthyl or biphenyl which may optionally carry substituents selected from the group consisting of halogen, nitro, cyano, lower alkyl, lower alkoxy, aryloxy, arylmercapto, carboxy, carbamoyl and lower acylamino groups, or $R_7$ is a furyl, thienyl, isoxazolyl, isothiazolyl or pyridyl group linked through a carbon atom, and $R_8$ is hydrogen, halogen, lower alkoxy, phenoxy or cyano, a protected amino such as an acylated amino, or lower alkylsulfonyl, arylsulfonyl, loweralkylamino-sulfonyl, arylaminosulfonyl bis(lower alkyl or aryl) aminosulfonyl, morpholinosulfonyl, (lower alkyl, aryl, aryloxy, lower alkoxy, lower alkylamino or arylamino) carbamoyl, (lower alkyl or aryl) sulfonamido, morpholinocarbonyl, (lower alkyl or aryl) sulfonaminocarbonyl, di(- lower alkyl) phosphonyl, di(aryl) hosphonyl, di(aryl-loweralkyl) phosphonyl, (aryl, lower alkyl) phosphonyl, (aryl, aralkyl) phosphonyl, (aralkyl, alkyl) phosphonyl, (lower alkyl or aryl or alralkyl)-alkylphosphinyl, (lower alkyl or aryl or aralkyl)-arylphosphinyl or(lower alkyl or aryl or aralkyl)-aralkylphosphinyl group. In this respect, it is observed that acids having a $pK_a$ in water of 5 or lower give good results in the reaction with the isocyanates in the presence of the catalysts of the present invention. Generally, speaking, when the acids employed are weak acids it is advantageous to use as catalyst a strong base, and with strong acids a weak base as catalyst. An example of a suitable acid is phenoxyacetic acid.

The penicillins and cephalosporins obtained by the process of the invention may be isolated as such from the reaction mixture in a manner known per se. The ester obtained may be converted into the free acid of a salt thereof such as an alkali, ammonium or amine salt suitable for incorporation in pharmaceutical compositions.

The N-substituted-6-aminopenicillanic acid and 7-aminocephalosporanic acid derivatives obtained according to the process of the invention have antibiotic properties, which make them useful as medicines for men and animals and as additives to animal feedstuffs. They are preferably employed for therapeutic purposes in the form of a non-toxic pharmaceutically acceptable salt such as the sodium, potassium or calcium salt. Other suitable salts for pharmaceutical preparations include salts with organic bases such as amines, for example, trialkylamines, procaine and dibenzylamine.

In the following examples there are described several preferred embodiments to illustrate the invention. However, it should be understood that the invention is not intended to be limited to the specific embodiments.

EXAMPLE I

Influence of catalysts on the reaction of the trimethylsilyl ester of 6-isocyanato-penicillanic acid with phenoxyacetic acid.

In all runs of the following Table, 3.14 g (10 mmol) of the isocyanate and 1.52 g (10 mmol) of phenoxyacetic acid were reacted at room temperature. The amount of solvent was 11.6 ml of toluene, or 12 ml of methylene chloride (i.e. dichloromethane). The amount of catalyst used was 0.05 ml in all runs. For the conversions, toluene was used as a clear solution of accuracy determined isocyanate content which was obtained directly from the reaction of disilylated 6-aminopenicillanic acid and phosgene. Pure crystalline isocyanate, obtained by precipitation from a solution in toluene concentration in vacuo, was employed for the conversions in methylene chloride. The conversion yields were determined microbiologically with a Bacillus subtilis on agar plates after dilution of the reaction mixture with ethyl acetate to 100 ml of which 1 ml was diluted with a buffer to 100 ml.

| solvent | catalyst | reaction time | % yield |
| --- | --- | --- | --- |
| toluene | none* | 6 hours | 7 |
| toluene | quinoline | 6 hours | 22 |
| toluene | triethylamine | 6 hours | 50.5 |
| toluene | collidine | 6 hours | 63.5 |
| toluene | pyridine | 6 hours | 63.5 |
| toluene | 1-methyl-imidazole | 2 hours | 69 |
| toluene | 1-isopropyl-benzimidazole | 6 hours | 74.5 |
| methylene chloride | pyridine | 6 hours | 51.5 |
| methylene chloride | 1-isopropyl-benzimidazole | 6 hours | 61 |

*Addition of 0.05 ml of 1-isopropyl-benzimidazole to the reaction mixture stirred for 6 hours without catalyst resulted in a yield of 35% after a second 6 hours of stirring, indicating that the non-catalyzed reaction was not only incomplete after six hours, but also produced poor yields of penicillin V.

EXAMPLE II

Influence of added catalysts on the reaction of the trimethylsilyl ester of 6-isocyanatopenicillanic acid with D-N-carbobenzoxy-phenylglycine.

In all runs of the following Table, 2.50 g (7.96 mmol) of the isocyanate and 2.30 g (8.07 mmol) of D-N-carbobenzoxy-phenylglycine were reacted at room temperature. The amount of methylene chloride was 25 ml and the employed amount of catalyst was in all runs approximately 0.6 mmol. After the reactions were finished (0.5 to 8 hours depending on the catalyst), the reaction mixtures were poured into cold acetone containing a small amount of water. The solvent mixture was then removed in vacuo and the residue was dissolved in cold ethyl acetate. The resulting solution was poured into ice-water and the pH was adjusted to 7. The layers were separated and the aqueous layer was extracted once with diethyl ether. The aqueous layer was then acidified to a pH of 3.8 and extracted with a 1:1 mixture of ethyl acetate and diethyl ether. 1 ml from the combined extracts diluted with ethyl acetate to 150 ml was diluted with buffer to 100 ml and the content of this solution was determined microbiologically with *Bacillus subtilis* 6633 on agar plates.

The purification procedure, carried out to minimize possible disturbing effects in the microbiological determination, caused an inevitable and unavoidable loss of the sensitive penicillin. Furthermore, as a number of fast rate inducing catalysts produce better yields at adjusted reaction temperature and changed relative amount, the relative order of effectiveness given below is only semi-quantitative and is only proportionally correct in the circumstances mentioned above. Qualitatively, the same trend was found upon comparison of thin-layer chromatograms taken directly from the reaction mixtures.

When pyridine was the catalyst, the yield of penicillin present in the extract was 32%. With 4-dimethylamino-pyridine as catalyst, a value of about 50% was found. The actual conversion yield found with column chromatography of the reaction product after treatment with aqueous acetone was better than 60% for 4-dimethylamino-pyridine as catalyst. When the yield of carbobenzoxyampicillin induced by pyridine is taken as the standard, the order of effectiveness is as follows:

| | |
|---|---|
| 0.44 | 1,5-diazabicyclo[4.30]-5-nonene |
| 1.00 | pyridine |
| 1.21 | 1:1 mixture of 5- and 6-nitro-1-methyl-benzimidazole |
| 1.57 | 1-methyl-imidazole |
| 1.63 | 4-methoxy-pyridine N-oxide . $H_2O$ |
| 1.65 | 1-benzyl-benzimidazole and 4-methoxy-pyridine |
| 1.67 | 4-methoxy-pyridine N-oxide (anhydrous) |
| 1.70 | 1-benzyl-imidazole |
| 1.73 | 4-dimethylamino-pyridine and 5-chloro-1-methyl-imidazole |
| 1.79 | 1-methyl-benzimidazole |
| 1.80 | 5-methoxy-1-phenyl-benzimidazole |
| 1.89 | imidazo[1,2-α]pyridine |

EXAMPLE III

Reaction of the trimethylsilyl ester of 6-isocyanato-penicillanic acid with 2'-carboxy-phenylacetic acid 3.14 g (10 mmol) of the trimethylsilyl ester of 6-isocyanato-penicillanic acid dissolved in 30 ml of dry benzonitrile were placed in a 100 ml three-necked vessel provided with a gas inlet tube through which nitrogen was introduced continuously, a dropping funnel and a gas outlet tube connected to a test tube containing baryta water. A solution of 1.80 g (10 mmol) of 2'-carboxyphenyl-acetic acid (homo-phthalic acid) and 0.9 ml (about 11 mmol) of 1-methylimidazole in 30 ml of benzontrile was added dropwise over a period of 75 minutes to the magnetically stirred solution. The rapid disengagement of carbon dioxide was discernible after about 5 minutes and continued during the addition period, but slowed down gradually during a period of about 60 minutes after completion of the addition, after which the solution was cooled down from room temperature to 0° C. 10 ml of cold acetone containing about 1 ml of water were added thereto annd extensive thin-layer tests showed that, in addition to the by-product N,N'-di-penicillanyl-urea (about 45%), there was formed only one penicillin (about 55%). The reaction mixture was poured into ice-water, followed by the addition of dilute sodium hydroxide until a pH of 6 was obtained. After separation of the layers, the aqueous layer was extracted twice with diethyl ether and acidified with dilute HCl to a pH of 4.0, and then was extracted three times with a 9:1 mixture of diethyl ether and ethyl acetate in order to get rid of unreacted homophthalic acid. The aqueous layer was then acidified to a pH of 3.0 and was extracted four times with diethyl ether in which at that pH the urea is practically insoluble. The combined ether extracts were washed twice with cold water, dried over anhydrous magnesium sulfate, filtered and evaporated to dryness. The obtained slightly yellow solid (yield about 45%) was submitted to PMR- and IR-spectra, which showed the presence of ether and a small amount of homophthalic acid as impurities and also that the product contained only one of the two possible penicillins. From the spectra, it was not possible to determine with absolute certainty a definite choice between the two possible structures. However, from the fact that, under similar circumstances, benzyl-penicillin is formed in about 45% yield from phenylacetic acid, while phenyl-penicillin is formed in less than 10% yield of benzoic acid, it is reasonable to assume, that the obtained penicillin is ortho-carboxybenzyl-penicillin of the formula:-

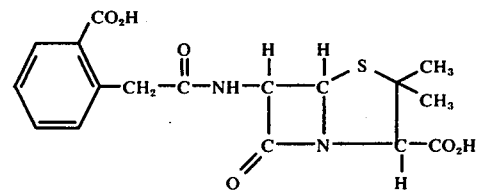

The following Example illustrates the fact that the new catalysts of the invention can be used in the reaction of other types of isocyanates with carboxylic acids to increase the yield of amide product.

EXAMPLE IV

Influence of added catalysts on the reaction of phenyl-isocyanate with phenylacetic acid into N-phenyl-phenylacetamide.

3.57 g (30 mmol) of phenyl isocyanate, 4.08 g (30 mmol) of phenylacetic acid and 50 ml of methylene chloride (solvent) were employed in all runs carried out at room temperature, and the amount of catalyst used was in all runs 3 mmol. During the reactions, N-phenyl-phenylacetamide and/or diphenylurea partly precipitated from the initially clear solution. After the evolution of carbon dioxide had ended, aqueous acetone was added until the precipitated material was completely dissolved. From this solution, one ml was taken and mixed with an excess of carbon tetrachloride. The solution of carbon tetrachloride was evaporated under reduced pressure and the residue consisting of solid amide, urea, phenylacetic acid and catalyst was dissolved in hexadeuterio dimethylsulfoxide.

PMR-spectra were taken from the solutions in dimethylsulfoxide and the yield of N-phenyl-phenylacetamide was determined by comparison of the integral of the areas of the $CH_2$-signals belonging to N-phenyl-phenylacetamide and phenylacetic acid. The results were as follows:

| Catalyst | Yield (%) of amide |
|---|---|
| none | 22 |
| pyridine | 47 |
| 4-methoxy-pyridine N-oxide (anhydrous) | 58 |
| 1-vinyl-imidazole | 59 |
| imidazo-[1,2-α]pyridine | 59 |
| 4-methoxy-pyridine | 61 |
| *4-methoxy-pyridine N-oxide, 1 $H_2O$ | 62 |
| *4-methoxy-pyridine N-oxide, ½ $C_2H_5OH$ | 62 |
| 1-methyl-benzimidazole | 66 |
| *1-methyl-imidazole | 75 |
| *4-dimethylamino-pyridine | 83 |

*with these catalysts relatively short reaction times were noticed.

Various modifications of the process of the invention may be made without departing from the spirit or scope thereof and it should be understood that the invention is intended to be limited only as defined in the appended claims.

We claim:

1. A process for the preparation of acylamides comprising reacting an isocyanate compound of the formula

wherein Z is selected from the group consisting of alkyl of 1 to 7 carbon atoms, phenyl, naphthyl, cycloalkyl of 5 to 8 carbon atoms and mono- and binuclear heterocycles containing one or more heteroatoms selected from the group consisting of oxygen, nitrogen and sulphur, optionally substituted with at least one members selected from the group consisting of halogen atom, a nitro-, cyano-, phenoxy-, alkoxy- and alkylmercapto having 1 to 7 carbon atoms, phenylmercapto, esterified carboxyl, esterified hydroxyl, acylamino and a carbamoyl- group optionally substituted with alkyl groups of 1 to 7 carbon atoms, phenyl and phenylalkyl, with a carboxylic acid of the formula

wherein Z' is an hydrocarbon optionally substituted with at least one substituent less reactive with the isocyanato compound than the carboxyl group, with the carbon atom α-to the carboxyl group being saturated, in the presence of at least one catalyst of the formula

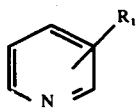

wherein R is at least one electron releasing group selected from the group consisting of alkoxy of 1 to 7 carbon atoms, phenoxy, phenyl lower alkoxy, silyloxy, di lower alkylamino and silyl lower alkylamino of 1 to 7 carbon atoms and disilylamino with the proviso that there are not electron releasing groups in both the 2- and 6-positions and n is 1, 2 or 3 and N-oxides thereof.

2. Process according to claim 1, characterized in that compounds of the formulae:-

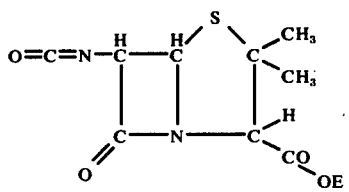

or

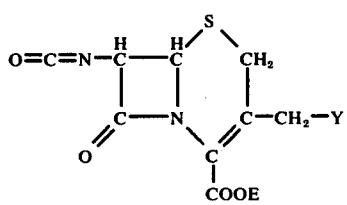

wherein E represents an easily removable protecting group which does not interfere with the reactions and wherein Y represents a hydrogen atom, an acyloxy or a protected hydroxy group are reacted with the carboxylic acid

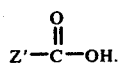

3. Process according to claim 2 characterized in that the reaction is carried out at temperatures between −10° to 50° C.

4. A process of claim 1 wherein the isocyanato compound is selected from the group consisting of an ester of 6-isocyanato penicillanic acid and an ester of 7-isocyanato cephalosporanic acid and the carboxylic acid has the formula

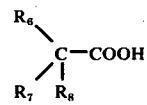

wherein $R_6$ is selected from the group consisting of hydrogen, alkyl of 1 to 7 carbon atoms and halogen, $R_7$ is selected from the group consisting of hydrogen, alkyl of 1 to 7 carbon atoms, cycloalkyl of 5 to 8 carbon atoms, phenyl and naphthyl optionally substituted with a member selected from the group consisting of halogen, nitro, cyano, alkyl of 1 to 7 carbon atoms, alkoxy of 1 to 7 carbon atoms phenoxy, phenyl mercapto, carboxy, carbamoyl and acylamino of 2 to 8 carbon atoms in the hydrocarbons, furyl, thienyl, isoxazolyl, isothiozolyl, or pyridyl linked through a carbon atom, and $R_8$ is selected from the group consisting of hydrogen, halogen, alkoxy of 1 to 7 carbon atoms, phenoxy, cyano, acylated amino, alkylsulfonyl, phenylsulfonyl, naphthalysulfonyl, alkylaminosulfonyl, phenylaminosulfonyl, bis (alkyl or phenyl) aminosulfonyl, morpholinosulfonyl, alkyl, phenyl, phenoxy, alkoxy, alkylamino or phenylamino) carbamoyl, (alkyl or phenyl) sulfonamido, morpholinocarbonyl and (alkyl or phenyl) sulfonylaminocarbonyl di(alkyl) phosphonyl, di(phenyl) phosphonyl, di(phenyl, alkyl) phosphonyl, (phenyl, alkyl) phosphonyl, (phenyl, phenyl-alkyl) phosphonyl, (phenyl-alkyl, alkyl) phosphonyl, (alkyl or phenyl or phenylalkyl) alkylphosphinyl, (alkyl or phenyl or phenylalkyl) phenylphosphinyl or (alkyl or phenyl or phenylalkyl) phenylalkylphosphinyl group, the alkyls containing 1 to 7 carbon atoms.

5. The process of claim 2 wherein the acid has a pKa in water of 5 or below.

6. The process of claim 1 wherein the catalyst has the formula

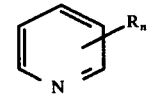

wherein n is 1 to 3 and R is selected from the group consisting of methoxy, phenoxy, benzyloxy and dimethylamino and the N-oxides thereof.

7. The process of claim 6 wherein the catalyst is selected from the group consisting of 4-methoxypyridine, 4-dimethylaminopyridine and 4-methoxypyridine-N-oxide.

8. The process of claim 1 wherein the catalyst is not an N-oxide and the reaction is effected in an inert organic solvent.

9. The process of claim 1 wherein the catalyst is an N-oxide and the reaction is effected in the presence of a trace of water.

10. The process of claim 9 wherein the catalyst is an N-oxide with water of crystallization bound thereto.

* * * * *